(12) United States Patent
Hershcovitz-Fundoiano et al.

(10) Patent No.: US 10,238,766 B2
(45) Date of Patent: Mar. 26, 2019

(54) DIAGNOSTIC COMPOSITION FOR IDENTIFYING AMNIOTIC FLUID

(71) Applicant: COMMON SENSE LTD., Caesarea (IL)

(72) Inventors: Yifat Hershcovitz-Fundoiano, Karkur (IL); Vered Pardo-Yissar, Neve Monoson (IL); Hadar Kessary Shoham, Zichron Yaakov (IL)

(73) Assignee: Common Sense Ltd., Caesarea (IL)

( * ) Notice: Subject to any disclaimer, the term of this patent is extended or adjusted under 35 U.S.C. 154(b) by 100 days.

(21) Appl. No.: 15/321,672

(22) PCT Filed: Jun. 30, 2015

(86) PCT No.: PCT/IL2015/050670
§ 371 (c)(1),
(2) Date: Dec. 22, 2016

(87) PCT Pub. No.: WO2016/001918
PCT Pub. Date: Jan. 7, 2016

(65) Prior Publication Data
US 2017/0197007 A1    Jul. 13, 2017

Related U.S. Application Data

(60) Provisional application No. 62/019,439, filed on Jul. 1, 2014.

(51) Int. Cl.
*G01N 21/75* (2006.01)
*A61L 15/56* (2006.01)
*A61F 13/42* (2006.01)
*A61L 15/48* (2006.01)
*A61B 10/00* (2006.01)
(Continued)

(52) U.S. Cl.
CPC .......... *A61L 15/56* (2013.01); *A61B 10/0048* (2013.01); *A61F 13/42* (2013.01); *A61L 15/48* (2013.01); *G01N 21/80* (2013.01); *G01N 33/84* (2013.01); *A61B 2010/0074* (2013.01); *A61F 2013/422* (2013.01)

(58) Field of Classification Search
CPC ......... A61L 15/56; A61L 15/48; G01N 33/84; G01N 21/80; A61B 10/0048; A61B 2010/0074; A61F 13/42; A61F 2013/422
See application file for complete search history.

(56) References Cited

U.S. PATENT DOCUMENTS 5,897,834 A    4/1999    Lawrence et al.
6,126,597 A    10/2000   Smith et al.
6,149,590 A    11/2000   Smith et al.
(Continued)

FOREIGN PATENT DOCUMENTS

CN     101813702 A       8/2010
WO     WO-2009/114579 A2 9/2009

OTHER PUBLICATIONS

International Search Report and Written Opinion from PCT International Application No. PCT/IL2015/050670 dated Oct. 14, 2015.

*Primary Examiner* — Dennis White
(74) *Attorney, Agent, or Firm* — Foley Hoag LLP; Alexander Akhiezer; Janine S. Ladislaw (57) ABSTRACT

The present invention relates to the field of medical diagnostics and more specifically, to identification of amniotic fluid.

20 Claims, 3 Drawing Sheets

Dark stain (51) Int. Cl.
*G01N 21/80* (2006.01)
*G01N 33/84* (2006.01)

(56) References Cited

U.S. PATENT DOCUMENTS

| | | |
|---|---|---|
| 6,562,297 B1 | 5/2003 | Bonstein et al. |
| 6,627,394 B2 | 9/2003 | Kritzman et al. |
| 6,719,691 B2 | 4/2004 | Kritzman et al. |
| 6,921,647 B2 | 7/2005 | Kritzman et al. |
| 7,314,752 B2 | 1/2008 | Kritzman et al. |
| 7,541,177 B2 | 6/2009 | Kritzman et al. |
| 7,947,467 B2 | 5/2011 | Kritzman et al. |
| 8,097,433 B2 | 1/2012 | Brusilovsky et al. |
| 8,114,610 B2 | 2/2012 | Fuks et al. |
| 2003/0017605 A1 | 1/2003 | Kritzman et al. |
| 2007/0134740 A1 | 6/2007 | Brusilovsky et al. |
| 2008/0254441 A1 | 10/2008 | Mohammed |
| 2010/0136707 A1* | 6/2010 | Kritzman ........... A61B 5/14539 436/163 |

* cited by examiner

DIAGNOSTIC COMPOSITION FOR IDENTIFYING AMNIOTIC FLUID

FIELD OF THE INVENTION

The present invention relates to the field of medical diagnostics and more specifically, to identification of amniotic fluid.

BACKGROUND OF THE INVENTION

Premature rupture of the amniotic sac is a common disorder that happens to occur in around 10% of pregnant women. Failure to treat premature rapture may cause intra-amnion infection, disruption in fetal lung development and even perinatal death.

Several approaches for detecting amniotic leakage are known in the art, including chromatographic detection of a color change in a diagnostic article following contact with vaginal secretion.

A number of devices involving panty shields, swabs and the like, with indicators aimed to identify amniotic fluid were developed, for example, in U.S. Pat. Nos. 5,897,834; 6,126,597 and 6,149,590. These devices can be worn, or otherwise used, by the user and whenever there is a secretion it is absorbed and further detected.

U.S. Pat. No. 6,921,647 and Continuation-in-Parts thereof, including, U.S. Pat. Nos. 7,314,752; 7,541,177 and 7,947,467 disclose secretion-monitoring article for identifying a secreted biological fluid, including, amniotic fluid, comprising: a body that includes an absorbent material and an indicator system having at least one pH determining member. The pH determining member includes a chemical composition which reacts with fluids containing urea differently than with fluids that do not contain urea, in a manner such that the former can be distinguished from the latter while avoiding false positive indications. The pH determining member may further, or alternatively, include a hydrophobic chemical composition that reacts with fluids based on the buffer capacity thereof, such that fluids having different buffer capacities can be distinguished.

It has been also proposed to detect the rupture of the amniotic sac by employing immunochemical analysis of the proteins in the amniotic fluid, such as, alpha-fetoprotein, prolactin, fibronectin, and insulin-like growth-factor binding protein 1. For example, U.S. Pat. No. 8,114,610 discloses a method of detecting amniotic fluid in a sample comprising a vaginal secretion of a pregnant woman using a combination of PAMG-1-specific monoclonal antibodies.

There is an unmet need for an improved diagnostic system that can differentiate between amniotic fluid and an interfering biological fluid, such as, urine, with minimal false positive results, while providing a reliable indication which is stable over time, and while reducing the amount of time required to get the reliable result.

SUMMARY OF THE INVENTION

The present invention discloses an indicator composition for detecting amniotic fluid in vaginal secretion comprising: a plurality of polymers; a plasticizer; a surfactant; an ion-balance reagent; an acid and an indicator agent, wherein said composition is devoid of a wetting agent. The present invention further discloses diagnostic articles for identifying amniotic fluid and methods of using same.

Advantageously, the articles of the invention may operate right after contacting the vaginal secretion. Specifically, the articles and diagnostic compositions disclosed herein do not require any drying time and/or do not require waiting for urine evaporation. Thus, detection of amniotic fluid (or other fluids) by the articles and compositions disclosed herein is a one-step process, namely, upon contact of liquid (amniotic fluid or urine) with an article comprising the diagnostic composition, detection can be carried out on the article as is, right after being in contact with the fluids. Without wishing to be bound by any theory or mechanism, it is assumed that this advantage is rendered by the unique combination of the ingredients in the diagnostic formulations of the invention, or may be specifically attributed to the lack of wetting agent, the presence of an aromatic carboxylic acid, the presence of an hydrophilic non-ionic polymer as surfactant, the presence of a tri-ester non-cyclic plasticizer or the combination thereof, together with the rest of the ingredients.

Furthermore, the articles of the invention enable initial self-detection and do not require the patient to visit healthcare professional in order to distinguish between positive and false-positives. Accordingly, using the article of the invention saves a significant amount of time required to determine if amniotic fluid is actually leaking.

In some embodiments, there is provided an indicator composition for detecting amniotic fluid in vaginal secretion comprising: a plurality of polymers; a non-cyclic plasticizer; a hydrophilic surfactant; an aromatic carboxylic acid; an ion-balance reagent and an indicator agent, wherein said composition is devoid of a wetting agent.

In some embodiments, said aromatic carboxylic acid comprises salicylic acid, benzoic acid or a combination thereof.

In some embodiments, the aromatic carboxylic acid is salicylic acid.

In some embodiments, the hydrophilic surfactant is a non-ionic surfactant.

In some embodiments, the hydrophilic surfactant is a polymer.

In some embodiments, the hydrophilic surfactant comprises a block copolymer surfactant.

In some embodiments, the indicator agent is negatively charged.

In some embodiments, the ion-balance reagent is a quaternary ammonium salt.

In some embodiments, the non-cyclic plasticizer is a tri-ester plasticizer.

In some embodiments, there is provided an indicator composition for detecting amniotic fluid in vaginal secretion consisting of a plurality of polymers; a non-cyclic plasticizer; a hydrophilic surfactant; an aromatic carboxylic acid; an ion-balance reagent and an indicator agent.

In some embodiments, there is provided an article for detecting amniotic fluid in vaginal secretion comprising: an absorbent material for absorbing a biological fluid secreted from a person, and an indicator composition, comprising: a plurality of polymers; a non-cyclic plasticizer; an hydrophilic surfactant; an aromatic carboxylic acid; an ion-balance reagent and an indicator agent, wherein said composition is devoid of a wetting agent.

In some embodiments, the absorbent material is selected from the group consisting of a swab, gauze, panty shield, hygienic napkin, diaper and interlabial absorbent structure.

In some embodiments, there is provided a method for diagnosing amniotic fluid leakage in vaginal secretion comprising:

(a) positioning a secretion-monitoring article to receive a biological fluid secreted from the subject, the article comprising an indicator composition comprising: a plurality of polymers; a non-cyclic plasticizer; an hydrophilic surfactant; an aromatic carboxylic acid; an ion-balance reagent and an indicator agent, wherein said composition is devoid of a wetting agent;

(b) contacting said article with vaginal secretion; and (c) viewing the article, wherein a color change indicates the presence of amniotic fluid.

In some embodiments, said color change is a dark stain relative to background of the secretion monitoring article. In some embodiments, the dark stain is a dark blue stain or a dark green stain.

In some embodiments, said viewing is performed within less than 10 minutes after said contacting. In some embodiments, said viewing is performed within less than 9 minutes after said contacting. In some embodiments, said viewing is performed within less than 8 minutes after said contacting. In some embodiments, said viewing is performed within less than 7 minutes after said contacting. In some embodiments, said viewing is performed within less than 6 minutes after said contacting. In some embodiments, said viewing is performed within less than 5 minutes after said contacting. In some embodiments, said viewing is performed within less than 4 minutes after said contacting. In some embodiments, said viewing is performed within less than 3 minutes after said contacting. In some embodiments, said viewing is performed within less than 2 minutes after said contacting.

In some embodiments, said indicator composition is consisting of a plurality of polymers; a non-cyclic plasticizer; a hydrophilic surfactant; an aromatic carboxylic acid; an ion-balance reagent and an indicator agent.

In some embodiments, there is provided a kit comprising the article for detecting amniotic fluid in vaginal secretion, and instructions for use.

In some embodiments, the kit further comprises a color scale presenting the color expected to appear upon contact of the article with amniotic fluid and the color expected to appear upon contact of the article with urine and any non-amniotic fluid.

Further embodiments, features, advantages and the full scope of applicability of the present invention will become apparent from the detailed description and drawings given herein after. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Exemplary embodiments are illustrated in referenced figures. It is intended that the embodiments and figures disclosed herein are to be considered illustrative rather than restrictive. The figures are listed below.

DETAILED DESCRIPTION OF THE INVENTION

The present invention provides an indicator composition, a diagnostic article comprising same, and methods of use thereof for obtaining an immediate, clear and reliable identification of amniotic fluid leakage.

The terms "amniotic fluid leakage" and "premature rupture of the amniotic sac" are interchangeable and relate to the spontaneous rupture of the membranes (the 'amniotic sac' is often termed 'fetal membrane') 24 or more hours before the onset of labor. About 30-50% of premature ruptures occur before the 37th week of pregnancy. As amniotic fluid leakage is associated with a significant increase in the risk of an intrauterine infection and disturbance of development of the fetal lung system, definitive and reliable diagnosis of the rupture is material. Intrauterine penetration of such infections increases both maternal and perinatal morbidity and mortality by about ten percent. Immediate diagnosis of a rupture at 38 to 40 weeks of pregnancy is crucial, since once detected delivery should be induced as soon as possible. The rupture diagnosis is also important before 37 weeks of pregnancy because it enables prevention of intra-amnion infection and the stimulation of fetal lung development.

Due to the severe consequences of amniotic fluid leakage, pregnant women undergo severe stress and often go to a health-care professional upon secretion of any liquid from the vicinity of the vagina. The health-care professional looks for the presence of amniotic fluid by checking the pH of the vaginal secretions—amniotic fluid is having a pH of between 6.7 and 7.5. Since pregnant women often have urinary incontinence and since urine typically has a pH of between 5.0 and 8.0, if only pH is checked, a false positive result may occur: urine being identified as amniotic fluid. Consequently, it is necessary that a vaginal secretion be examined using a microscope for the presence of a fern-shaped pattern indicative of amniotic fluid.

As the time between the fluid secretion and the arrival at the health-care professional may be long, there is often no evidence of amniotic fluid upon examination. The secretion may mistakenly assumed to be urine, which may result with tragic consequences. On the other hand, the healthcare professional may decide to err on the side of caution, misdiagnosing the secretion of urine as amniotic fluid leading to an unnecessary hospitalization and patient stress.

Various diagnostic indicators are known, however, an obstacle of many is that they often provide "false positives" due to changes in pH on drying, interfering biological fluids and repetitive cycles of drying/wetting. The "false positive" readings can be stressful and time consuming to the user. A device that minimizes these "false positive" readings is disclosed herein. The present invention is an improvement over the prior art, providing a diagnostic composition which is more accurate, reliable and convenient for the user. The diagnostic composition of the present invention comprises an indicator agent that identifies the pH associated with the fluid, a plurality of polymers, a tri-ester non-cyclic plasticizer, hydrophilic non-ionic polymer surfactant, an ion-balance reagent and at least one aromatic carboxylic acid, wherein said composition is devoid of a wetting agent.

As used herein and in the claims the term "plurality" means at least two.

In some embodiments, there is provided an indicator composition for detecting amniotic fluid in vaginal secretion comprising: a plurality of polymers; a non-cyclic plasticizer; a hydrophilic surfactant; an aromatic carboxylic acid; an ion-balance reagent and an indicator agent, wherein said composition is devoid of a wetting agent.

In some embodiments there is provided an indicator composition for detecting amniotic fluid in vaginal secretion comprising: a plurality of polymers; a tri-ester non-cyclic plasticizer; a hydrophilic non-ionic polymer surfactant; an aromatic carboxylic acid; an ion-balance reagent and an indicator agent, wherein said composition is devoid of a wetting agent.

In some embodiments, the indicator composition is consisting of a plurality of polymers; a non-cyclic plasticizer; a hydrophilic surfactant; an aromatic carboxylic acid; an ion-balance reagent and an indicator agent.

In some embodiments, the indicator composition is consisting of a plurality of polymers; a tri-ester non-cyclic plasticizer; a hydrophilic non-ionic polymer surfactant; an aromatic carboxylic acid; an ion-balance reagent and an indicator agent.

In some embodiments there is provided an article for detecting amniotic fluid in vaginal secretion comprising: an absorbent material for absorbing a biological fluid secreted from a person, and an indicator composition comprising a plurality of polymers; a non-cyclic plasticizer; a hydrophobic surfactant; an aromatic acid; an ion-balance reagent and an indicator agent, wherein said composition is devoid of a wetting agent.

In some embodiments there is provided a method for diagnosing amniotic fluid leakage in vaginal secretion comprising:
(a) positioning a secretion-monitoring article to receive a biological fluid secreted from the subject, the article comprising: an absorbent material and an indicator composition comprising a plurality of polymers, an aromatic acid, a non-cyclic plasticizer, a hydrophobic surfactant, an ion-balance reagent and an indicator agent, wherein said composition is devoid of a wetting agent;
(b) contacting said article with vaginal secretion; and
(c) viewing the article, wherein a color change indicates the presence of amniotic fluid.

In some embodiments, contacting the article comprises removing release tapes covering adhesive strips, thereby exposing the adhesive strip, and placing the article in the crotch portion of an undergarment, thereby attaching said article to said crotch portion of the undergarment.

In some embodiments, viewing the color change comprises detecting dark staining on the article, wherein the dark staining is indicative of the presence of amniotic fluid.

In some embodiments, the dark staining is blue staining. In some embodiments, the dark staining is green staining.

The compositions described herein may be prepared by methods well known to those skilled in the art.

In some embodiments, said plurality of polymers comprises a first polymer and a second polymer, the hydrophobicity of said first polymer is higher than the hydrophobicity of said second polymer.

In some embodiments, said plurality of polymers comprises a first polymer and a second polymer having similar hydrophobicity. The terms "hydrophobic" and "hydrophilic" polymers refer on the amount of water vapor absorbed by the polymers at 100% relative humidity. Thus, "hydrophobic polymers" typically refer to polymers that absorb only up to 1 wt. % water at 100% relative humidity, while moderately hydrophilic polymers absorb 1-10% wt. % water and hydrophilic polymers are capable of absorbing more than 10 wt. % of water. In some embodiments, the polymers of the invention are water-insoluble polymers. In some embodiments, each of the polymers comprises cellulose, derivatives thereof or copolymers thereof, including, without limitation, cellulose acetate, cellulose acetate butyrate, cellulose acetate phthalate, cellophane, cellulose nitrate, cellulose propionate, cellulose propionate butyrate, cellulose diacetate, cellulose triacetate, cellulose ethers, and carboxymethyl cellulose, and any copolymers and any blends of the aforementioned polymers.

In some embodiments, each polymer comprises cellulose, derivatives thereof or copolymers thereof.

In some embodiments, the polymers of the invention are cellulose esters comprising partially acetylated cellulose polymeric chains, including, but not limited to, cellulose acetate in which substantially each one of positions 2, 3 and 6 of the monomeric glucose units of the cellulose polymer, consists of either free hydroxyl or acetate. In some embodiments, the polymers are cellulose esters comprising substantially acetylated cellulose polymeric chains, including, but not limited to, cellulose triacetate. In some embodiments, the polymers are cellulose esters comprising partially esterified cellulose polymeric chains, wherein the esterification comprises partial acetylation and partial butyrilation, including, but not limited to, cellulose acetate butyrate, in which substantially each one of positions 2, 3 and 6 of the monomeric glucose units of the cellulose polymer consists of either free hydroxyl, acetate or butyrate. In some embodiments, the polymers are cellulose esters comprising partially esterified cellulose polymeric chains, wherein the esterification comprises partial acetylation and partial propionilation, including, but not limited to, cellulose acetate propionate, in which substantially each one of positions 2, 3 and 6 of the monomeric glucose units of the cellulose polymer consists of either free hydroxyl, acetate or propionate.

Without wishing to be bound by any theory or mechanism of action, the less hydrophobic polymer, is more hydrophilic thereby improves the penetration of the fluid to be tested, into the panty liner. In addition, the more hydrophobic polymer provides improved adhesion of the indicator composition to the absorbent carrier (e.g. the fabric) thereby minimizing or even avoiding leaching of the formulation components.

In some embodiments, said plurality of polymers comprises at least one polymer selected from the group of cellulose acetate and cellulose acetate butyrate.

In some embodiments, said plurality of polymers comprises a first polymer, such as, cellulose acetate butyrate, and a second polymer, such as, cellulose acetate, the hydrophobicity of said first polymer is higher than the hydrophobicity of said second polymer.

In some embodiments, the plasticizer is a low molecular weight plasticizer. Typically, a low molecular weight plasticizer is a plasticizer having a molecular weight of less than 600 gr/mol. In some embodiments, the plasticizer is having a molecular weight of less than 500 gr/mol. In some embodiments, the plasticizer is having a molecular weight of less than 400 gr/mol. In some embodiments, the plasticizer is having a molecular weight of less than 300 gr/mol.

Suitable low molecular weight plasticizers include alkyl and aryl phosphates, such as, tributyl phosphate, trioctyl phosphate, tricresyl phosphate, and triphenyl phosphate; alkyl citrate and citrate esters, such as, trimethyl citrate, triethyl citrate, tributyl citrate, acetyl triethyl citrate, and trihexyl citrate; dialkyladipates such as dioctyladipate (DOA; also referred to as bis(2-ethylhexyl)adipate), diethyl adipate, di(2-methylethyl)adipate, and dihexyladipate; dialkyl tartrates such as diethyl tartrate and dibutyl tartrate; dialkylsebacates such as diethyl sebacate, dipropylsebacate and dinonylsebacate; dialkyl succinates such as diethyl succinate and dibutyl succinate; alkyl glycolates, alkyl glycerolates, glycol esters and glycerol esters such as glycerol diacetate, glycerol triacetate (triacetin), glycerol monolactatediacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; acetylated monoglycerides and mixtures thereof.

In some embodiments, the plasticizers comprise low molecular weight plasticizers, including, but not limited to, alkyl citrate and citrate esters, such as, trimethyl citrate, triethyl citrate, tributyl citrate, acetyl triethyl citrate, and trihexyl citrate, acetylated monoglycerides and mixtures thereof.

In some embodiments, the non-cyclic plasticizer is a tri-ester plasticizer. In some embodiments, the low molecular weight plasticizers comprise a triester structure. Such plasticizers include, but are not limited to, alkyl citrate and citrate esters, such as, trimethyl citrate, triethyl citrate, tributyl citrate, acetyl triethyl citrate and trihexyl citrate. In some embodiments, the plasticizer is triethyl citrate. In some embodiments, the plasticizer is other than dibutyl phthalate. In some embodiments, the plasticizer is other than Hexamoll Dinch (1,2-cyclohexane dicarboxylic acid diisononyl ester).

In some embodiments, the non-cyclic plasticizer comprises triethyl citrate. In some embodiments, the amount of the surfactant is within the range of 1% to 10% (wt/wt), relative to the total weight of the solid components.

The term "solid components" or "total solids" as used herein refer to the all ingredients within each formulation, in the absence of solvent, in particular, water and/or acetone.

The term "surfactant" as used herein refers to one or more surfactants. In some embodiments, surfactants refer to a plurality of surfactants.

In some embodiments, the surfactant comprises a hydrophilic surfactant. In some embodiments, the hydrophilic surfactant is a polymer. In some embodiments, the surfactant comprises a block copolymer surfactant. In some embodiments, the polymeric surfactant comprises a tri-block copolymer surfactant. In some embodiments, the polymeric surfactant comprises poly(ethylene oxide) and/or copolymers thereof. In some embodiments, the polymeric surfactant comprises poly(propylene oxide) and/or copolymers thereof. In some embodiments, the block copolymer surfactant comprises copolymer of poly(ethylene oxide) and poly(propylene oxide) and/or copolymers thereof.

In some embodiments, the hydrophilic surfactant is a non-ionic surfactant. In some embodiments, the non-ionic surfactant comprise a non-ionic polymeric surfactant. In some embodiments, the surfactant is selected from the group of poloxamer, alkyl poly(ethylene oxide), copolymers of poly(ethylene oxide) and poly(propylene oxide), octylglucoside, decylmaltoside, cetyl alcohol, oleyl alcohol, cocamidemonoethanolamine (cocamide MEA), cocamidediethanolamine (cocamide DEA), cocamidetriethanolamine (cocamide TEA), polysorbate, such as, Tween® (e.g. Tween 20® or Tween 80®), lecithin and combinations thereof.

In some embodiments, the non-ionic polymeric surfactant is selected from the group of poly(ethylene oxide) and copolymers of poly(ethylene oxide), poly(propylene oxide), polysorbate, such as, Tween® (e.g. Tween 20® or Tween 80®) and combinations thereof.

In some embodiments, the surfactant comprises poloxamer, polysorbate and a combination thereof.

In some embodiments, the surfactant comprises a poloxamer. In some embodiments, the surfactant comprises poloxamer 407.

In some embodiments, the surfactant comprises a polysorbate. In some embodiments, the non-ionic surfactant is other than ionic surfactants, such as, aliquot 336.

The term "poloxamer" as used herein refers to nonionic triblock copolymers comprising a central hydrophobic chain of polyoxypropylene (poly(propylene oxide)) and two hydrophilic chains of polyoxyethylene (poly(ethylene oxide)). Poloxamers are commonly termed "P" followed by three digits, the first two times 100 refer to the estimated molecular mass of the polyoxypropylene core, and the last digit times 10 is the percentage polyoxyethylene content. For example, P407 refers to a poloxamer with a polyoxypropylene molecular mass of 4,000 g/mol and 70% polyoxyethylene content.

The term "polysorbate" as used herein generally refers to polyoxyethylene derivative of sorbitan monolaurate. Common commercial brand names for polysorbates include Tween®, such as, Tween 20® or Tween 80®. The number following the polyoxyethylene part refers to the total number of oxyethylene groups found in the molecule. The number following the polysorbate part is related to the type of fatty acid associated with the polyoxyethylene sorbitan part of the molecule. Monolaurate is indicated by 20, monopalmitate is indicated by 40, monostearate by 60 and monooleate by 80.

Without wishing to be bound by any theory or mechanism, the non-ionic polymeric surfactant distributes within the urine and as a result retention time of urine is reduced thereby avoiding false positive results from urine.

In some embodiments, the at least one carboxylic acid comprises at least one unsubstituted or substituted carbocyclic or heterocyclic carboxylic acid. In some embodiments, the at least one carboxylic acid comprises at least one of unsubstituted or substituted aromatic or heteroaromatic carboxylic acid. In some embodiments, the at least one carboxylic acid comprises at least one unsubstituted or substituted aromatic carboxylic acid. In some embodiments, the at least one substituted carboxylic acid is selected from the group consisting of salicylic acid, benzoic acid, phthalic acid, terephthalic acid, isophthalic acid, α-naphthoic acid, β-naphthoic acid, isomers of toluic acid, isomers of halobenzoic acid, such as, but not limited to p-fluorobenzoic acid and m-chlorobenzoic acid, isomers of nitrobenzoic acids, isomers of trifluoromethylbenzoic acid, isomers of aminobenzoic acid, such as, but not limited to, anthranilic acid, isomers of anisic acid, m-hydroxybenzoic acid and p-hydroxybenzoic acid. Each possibility represents as separate embodiment of the present invention.

The term "isomer" as used herein refers to a positional isomer, denoting a relative location in which two or more substituents are located on the aromatic ring.

In some embodiments, the acid is an aromatic carboxylic acid. In some embodiments, the aromatic carboxylic acid is in the form of Ar—COOH. In some embodiments, Ar is selected from the group consisting of aryl and heteroaryl rings, wherein Ar is unsubstituted or substituted. Non limiting examples of substitutions include halogen, haloalkyl, $C_1$-$C_4$ alkyl, aryl, heterocyclyl, hydroxy, alkoxy, aryloxy, alkylaryloxy, heteroaryloxy, oxo, cycloalkyl, phenyl, heteroaryl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio, arylthio, or $C_1$ to $C_{10}$ alkylsulfonyl groups. Any substituent can be unsubstituted or further substituted with any one of these aforementioned substituents. Each possibility represents as separate embodiment of the present invention.

The terms "aryl" and "Ar" as used herein alone or as part of another group are interchangeable and denote an aromatic ring system containing from 6-14 ring carbon atoms. The aryl ring can be a monocyclic, bicyclic, tricyclic and the like. Non-limiting examples of aryl groups are phenyl, naphthyl, including, 1-naphthyl and 2-naphthyl, and the like. The aryl group may be unsubstituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. The heteroaryl generally contains 5 or more ring atoms. The heteroaryl group can be monocyclic, bicyclic, tricyclic and the like. Also included in this expression are the benzoheterocyclic rings and other fused heterocyclic ring systems. If nitrogen is a ring atom, the present invention also contemplates the N-oxides of the nitrogen containing heteroaryls. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group may be substituted through available atoms with one or more groups defined hereinabove for alkyl.

The terms "heterocyclic ring" or "heterocyclyl" used herein alone or as part of another group denote a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated. Preferred heterocyclic rings include piperidinyl, pyrrolidinyl, pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The term "halogen" used herein alone or as part of another group includes chloro, fluoro, bromo, and iodo.

In some embodiments, the at least one carboxylic acid comprises at least one carboxylic acid having a pKa smaller than 3. In some embodiments, the at least one carboxylic acid comprises at least one carboxylic acid having a water solubility of less than 100 gr/L. In some embodiments, the at least one carboxylic acid comprises at least one carboxylic acid having a water solubility of less than 10 gr/L. In some embodiments, the at least one carboxylic acid comprises at least one carboxylic acid having a water solubility of less than 5 gr/L.

In some embodiments, the aromatic carboxylic acid is selected from the group consisting of salicylic acid, benzoic acid and the like and combinations thereof. Each possibility represents as separate embodiment of the present invention.

In some embodiments, the aromatic carboxylic acid is salicylic acid.

In some embodiments, the aromatic carboxylic acid is other than non-aromatic carboxylic acids, such as, lactic acid, oxalic acid or citric acid. In some embodiments, the at least one carboxylic acid is other than citric acid.

Without being bound by any theory or mechanism, the aromatic carboxylic acid creates a complex, and may function as a trap, with the ammonium ions within the urine. This interaction results in reduction of interference from urine, including urine with pH level of 7.0 units, and even higher, and therefore improves indicator specificity.

In some embodiments, the ion-balance reagent is in an amount of about 0.1% to 2%. In some embodiments, the ion-balance reagent is present in an amount of about 0.1% to 1%; and the indicator agent is present in an amount of about 0.2% to 0.7%. In some embodiments, the ion-balance reagent is a quaternary ammonium ion. In some embodiments, the ion-balance reagent is a quaternary ammonium salt.

In some embodiments, the ion-balance reagent is selected from the group consisting of: di(long-chain alkyl)dimethyl ammonium chloride, N-methyl-N,N-bis(long-chain alkanoyloxyethyl)-N-(2-hydroxyethyl) ammonium methylsulfate, vinylbenzyldimethylcocoammonium chloride, methyl trioctyl ammonium chloride tricaprylylmethyl ammonium chloride, tridodecylmethyl ammonium chloride and cetyltimethyl ammonium chloride. Each possibility represents as separate embodiment of the present invention.

Any suitable ion-balance reagent may be used, including, tridodecylmethyl ammonium chloride (TDMAC; CAS 7173-54-8) or cetyltimethyl ammonium chloride (CTAC; CAS 112-02-7). In some embodiments, the ion balance reagent is a combination of ion-balance reagents. In some embodiments, the ion-balance reagent is TDMAC (Tridodecylmethylammonium chloride).

In some embodiments, the indicator is selected from the group of chemical compounds having negatively charged functional groups. In some embodiments, the indicator is a weak acid. In some embodiments, the indicator is selected from the group consisting of nitrazine yellow, thymol blue, bromothymol blue, xylenol blue, bromoxylenol blue, phenol red, m-cresol purple, chlorophenol red, bromocresol purple, alizarin, neutral red, and cresol red. Each possibility represents as separate embodiment of the present invention. A list of other suitable indicators can be found, for example, in U.S. Pat. No. 5,897,834. It is clear to one skilled in the art that the indicators specifically mentioned herein are just examples and any suitable indicators may be used.

In some embodiments, the indicator agent is selected from the group consisting of: cresol red, alizarin, bromocresol purple, chlorophenol red, nitrazine yellow, bromothymol blue, bromoxylenol blue, neutral red, phenol red, thymol blue, xylenol blue and m-cresol purple. Each possibility represents as separate embodiment of the present invention.

In some embodiments, the indicator agent is negatively charged.

In some embodiments, the indicator agent is a weak acid.

In some embodiments, the indicator agent comprises nitrazine yellow.

In some embodiments, the diagnostic composition is associated with an absorbent material, thereby forming a diagnostic article for absorbing the fluids secreted from a pregnant woman. The diagnostic article can be implemented using many devices and methods. In some embodiments, the article is implemented in a manner that can be easily used by non-skilled personnel, specifically a user. The body of the article comprising the absorbent material can be supplied to the user, for example, in the form of a pad, gauze, a swab, a fiber ball, but most preferably, as a sanitary napkin, diaper, panty shield, and interlabial structure.

In some embodiments, the article further comprises a means for mounting the article to facilitate the collection of the secreted biological fluid. An example of a mounting means includes, but is not limited to, adhesive strips associated with the article. In some embodiments, the article further comprises release tapes, each covering each of the adhesive strips. Covering as used herein also means protecting (e.g. from drying out). Typically, the user removes the release tapes to expose the adhesive strips of the article and places the article in the crotch portion of their undergarment, thereby preventing the article from moving out of position during regular use. Types of adhesive compounds that can be used are well known in the art.

In some embodiments, the diagnostic composition provides a visible indication of amniotic fluid. In some embodiments, the visual indication is stable for about a week.

The terms "stable indication" and "irreversible indication" are interchangeably used herein to describe an indication, typically a color indication, that once obtained remains sufficiently unaltered for the time required for clinical examination by a professional. Preferably, the color change is stable for at least 48 hours, more preferably at least 72 hours, and in some embodiments, preferably the color change is stable for about a week.

In some embodiments, the absorbent material is selected from the group consisting of a swab, gauze, panty shield, hygienic napkin, diaper and interlabial absorbent structure. Each possibility represents as separate embodiment of the present invention.

In some embodiments, there is provided a kit comprising the article for detecting amniotic fluid in vaginal secretion, and instructions for use of the article in order to detect amniotic fluid in vaginal secretion.

In some embodiments, the kit further comprises a color scale presenting the color expected to appear upon contact of the article with amniotic fluid and the color expected to appear upon contact of the article with urine.

In some embodiments, the kit comprises a plurality of article for detecting amniotic fluid in vaginal secretion.

In some embodiments, each article within the kit is separately wrapped.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1: Clinical Study

Samples of urine and amniotic fluid were collected from 83 pregnant women, according to the following distribution: urine and amniotic fluid were collected from 8 women, urine only was collected from 63 women, and amniotic fluid was collected from 12 women.

The inclusion criteria for subject participation in the study are pregnant women:
(i). Pregnant women 18 years to 50 years of age.
(ii). Subject is ready to sign the informed consent form.
(iii). Subject arrives at delivery room undergo amniotomy.

The exclusion criteria for subject participation in this study are:
(iv). Subject suffers from bleeding.
(v). Subject is unable or unwilling to cooperate with study procedures.
(vi). Subject is currently participating in another clinical study.

Subjects arriving at the delivery room were requested to collect a random urine sample in a clean container. Amniotic fluid samples were collected, by the clinician, during the amniotomy procedure. Each fresh urine and amniotic fluid sample in the study was tested using the test devices (panty liners) each comprising candidate formulation or a reference formulation, as follows:
1. Dipstick for pH and other urine parameters (using Combur-Test® strips, Roche Diagnostics).
2. 100 μl of amniotic fluid was dropped onto each device candidate and reference devices (AL-SENSE and AmniScreen).
3. 400 μl of urine was dropped onto each device candidate (a panty liner containing one of the eight candidate formulations) and each reference device (a panty liner containing the AmniScreen or Al-Sense formulations).
4. The study coordinator stirred each panty liner in a way that will mimic the "real life" usage.
5. For the amniotic fluid and urine samples, the coordinator recorded the result status (positive or negative) immediately (0-2 min), and after 5 min, 10 min, 15 min, 20 min, 30 min, 60 min and 120 min, based on the color observed on the tested pads. A positive result is concluded when the yellow panty liner show a blue, green stain of any size or shape, even if as a light color. A negative result is concluded when the panty liner color remained yellow.

Eight types of device candidates (Table 1) and two reference devices, AL-SENSE and AmniScreen (Table 2), were used. The ingredients in each candidate and reference formulations were dissolved in 50 ml acetone and 2 ml water.

TABLE 1

| | Formulations of candidate devices | | | | | | | |
| --- | --- | --- | --- | --- | --- | --- | --- | --- |
| | ALM1/ALM1G§ | | ALM2/ALM2G§ | | ALM3/ALM3G§ | | ALM4/ALM4G§ | |
| Agent | Wt. (g) | wt/wt(%) | Wt. (g) | wt/wt(%) | Wt. (g) | wt/wt(%) | Wt. (g) | wt/wt(%) |
| Cellulose acetate | 2 | 44.6 | 2 | 45.7 | 2 | 45.7 | 2 | 45.8 |
| Cellulose acetate-butyrate | 0.8 | 17.9 | 0.8 | 18.3 | 0.85 | 19.4 | 0.8 | 18.3 |
| Triethyl citrate | 1 | 22.3 | 1 | 22.8 | 1 | 22.8 | 1 | 22.9 |

TABLE 1-continued

Formulations of candidate devices

| Agent | ALM1/ALM1G[§] Wt. (g) | wt/wt(%) | ALM2/ALM2G[§] Wt. (g) | wt/wt(%) | ALM3/ALM3G[§] Wt. (g) | wt/wt(%) | ALM4/ALM4G[§] Wt. (g) | wt/wt(%) |
|---|---|---|---|---|---|---|---|---|
| TDMAC | 0.053 | 1.2 | 0.053 | 1.2 | 0.053 | 1.2 | 0.046 | 1.1 |
| Poloxamer | 0.3 | 6.7 | | | | | | |
| Salicylic acid | 0.3 | 6.7 | | | 0.25 | 5.71 | | |
| Benzoic acid | | | 0.3 | 6.7 | | | 0.3 | 6.86 |
| Tween 80 | | | 0.2 | 6.7 | 0.2 | 4.57 | 0.2 | 4.58 |
| Nitrazine yellow | 0.024 | 0.54 | 0.024 | 0.55 | 0.024 | 0.55 | 0.024 | 0.55 |
| Total | 4.48 | 100 | 4.38 | 100 | 4.38 | 100 | 4.37 | 100 |

[§]G = contains glue between the layers as a part of the manufacturing process.

TABLE 2

AL-SENSE and AmniScreen Compositions

| Ingredient | AL-Sense | AmniScreen | Units |
|---|---|---|---|
| Cellulose Acetate | 1.6 | 1.5 | Gr |
| Cellulose acetate butyrate | 0.8 | | Gr |
| Dibutyl phthalate | | 1.07 | Ml |
| Hexamoll Dinch | 0.8 | | Ml |
| TDMAC | 0.0453 | | Gr |
| Aliquat 336 | | 0.23 | Ml |
| 2-ethoxyethanol | | 1.5 | Ml |
| Citric acid | 0.0112 | | Gr |
| Nitrazine Yellow | 0.0091 | 0.024 | Gr |

The values of the AmniScreen reference device in terms of sensitivity and specificity were as follows: efficacy of 84% specificity and 96% sensitivity AmniScreen provides final reading after 30 minutes. Significance level of findings was determined to be equal to, or lower than, 5%. All statistical analyses were performed using SAS v9.3 (SAS®, SAS Institute Cary, N.C. USA) software.

Results (stains) were detected at different time points. While accurate detection with 100% sensitivity was obtained by articles comprising the indicator composition of the invention within the first 2 minutes after contact with amniotic fluid (Table 3), it was required to wait 30 minutes and 10 minutes when using AmniScreen and AL-SENSE, respectively, in order to avoid false positive readings (i.e. staining by urine). This is because in AmniScreen and AL-SENSE a stain is obtained from non-specific staining (by urine), which requires some time (30 minutes in AmniScreen and 10 minutes in AL-SENSE) to fade.

The results from the different tests, based on the pads color, were designated "Positive", "Negative". The term "Positive" means a blue stain, which appeared upon the yellow background of the panty liner device. The term "Negative" means that a stain did not appear, or appeared and faded back to yellow during detection time. A stain formed in a urine test was considered as false positive and when a stain does not appear in a urine test it was true negative. Similarly, when a stain did not appear in a test of amniotic fluid it was referred to as false negative.

Figure 1:
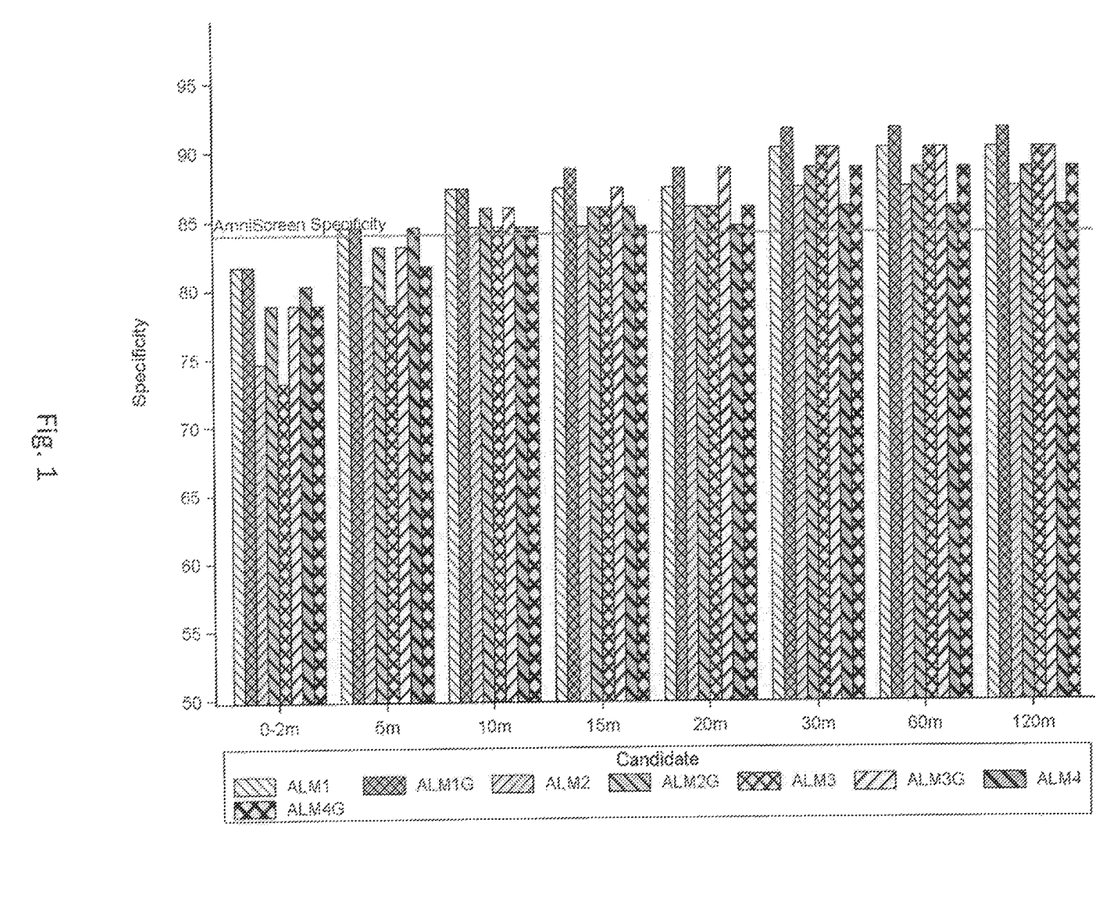
FIG. 1 shows the relative specificity of the articles disclosed herein (including ALM1 which is also termed "ALSENSE Blue") at the following time points: 0-2 min., 5 min., 10 min., 20 min., 30 min 1 hr. and 2 hrs.

Tables 3-4 and FIG. 1 present the detected results read from the candidate devices following exposure to amniotic fluid (Table 3) or to urine (Table 4). Efficacy evaluation was obtained by comparing the sensitivity, i.e. the proportion of "Positive" readings upon exposure of the pads to amniotic fluid, and the specificity, i.e. the proportion of "Negative" upon exposure of the pads to urine, from the various devices (pads). The resulting sensitivities and specificities are presented in Tables 3 and 4 along with the respective two-sided 90% exact Confidence Intervals (CI) compared with McNemar's test. For each candidate device agreement between the candidate device and the AmniScreen was calculated together with 95% exact confidence intervals. Agreements in amniotic fluid, in urine and altogether were evaluated as the percentage of equal diagnoses (positive-positive negative-negative) between pairs of devices. The devices diagnosis agreement levels were cross-tabulated against those of the AmniScreen overall agreement levels and compared using McNemar's test. As shown in Table 3 all candidate devices had a sensitivity of 100%, i.e. all candidates exhibited a positive reading (blue stain) following exposure to amniotic fluid. Furthermore, in all candidate pads the color change (blue stain formation on a yellow background) occurred immediately or by no longer than two minutes after contacting the test sample (i.e. 0-2 min) and remained stable for the duration of the two-hour follow-up. Regarding specificity, candidate pads ALM1 and ALM1G demonstrated superiority over the remaining candidate pads (Table 4 and FIG. 1). These two candidates exhibited 84% specificity at 5 minutes and even better specificity values at 10 minutes with no fluctuations: Specificity of the ALM1 (and ALM1G) candidate at 5 minutes was 84.5% (60/71) and at 10 minutes 87.2% (62/71). Thus, ALM1 and ALM1G meet the goal of good accuracy in a short time span.

Tables 5 and 6 present the sensitivity and specificity, respectively, of five selected candidate pads, at 5 and 10 minutes along with the results of AL-SENSE and AmniScreen with lower two-sided 90% exact confidence bounds, based on the values presented in Tables 3 and 4. According to Table 5, the sensitivity of ALM1 at 5 and 10 minutes is 100% (namely, all amniotic fluid samples that were contacted with ALM1, resulted in a positive detection—blue stain). In terms of performance, it may be stated that for this study, the value of 86.09% has 95% confidence. Stated otherwise, the value of 86.09% refers to the assertion that may be made given the sample size and the sensitivity data. The same applies to AmniScreen. AL-SENSE has a 90% sensitivity, which is lower than that of ALM1 and AmniScreen.

TABLE 3

| Candidate device | 0-2 m | | 5 m | | 10 m | | 15 m | | 20 m | | 30 m | | 60 m | | 120 m | |
|---|---|---|---|---|---|---|---|---|---|---|---|---|---|---|---|---|
| | N | % | N | % | N | % | N | % | N | % | N | % | N | % | N | % |
| ALM1 | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |
| ALM2 | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |
| ALM3 | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |
| ALM4 | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |
| ALM1G | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |
| ALM2G | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |
| ALM3G | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |
| ALM4G | | | | | | | | | | | | | | | | |
| Positive | 20 | 100.0 | 20 | 100.0 | 20 | 100.0 | 20 | 100.0 | 20 | 100.0 | 20 | 100.0 | 20 | 100.0 | 20 | 100.0 |

'%'—% sensitivity; 'N'—the number of samples tested; 'm'—minutes.

According to Table 6, specificity of ALM1 at 5 minutes (84.51%) is better than that of AmniScreen (77.46%; p=0.0588) with a significant superiority at 10 minutes (87.32%) relative to AmniScreen (p=0.0082) and AL-SENSE (74.65%, p=0.0067). Specificities of AmniScreen and AL-SENSE were not significantly different (p=0.5637).

Specificity, as used herein refers, to correct negative reading, namely, non-staining of a composition upon contact thereof with a urine sample.

Figure 3A:
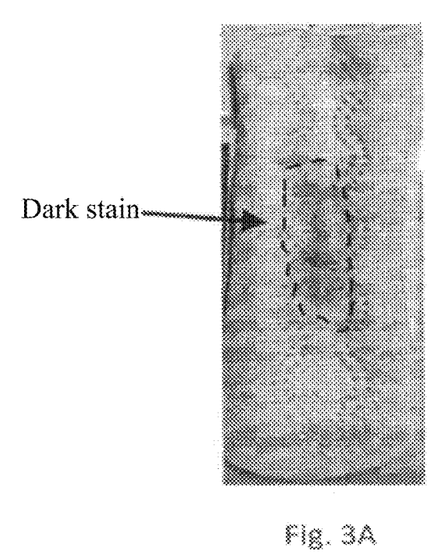
FIG. 3A demonstrates a photo of an absorbent article containing the ALM1 formulation 30 min following contact with amniotic fluid.
Figure 3B:
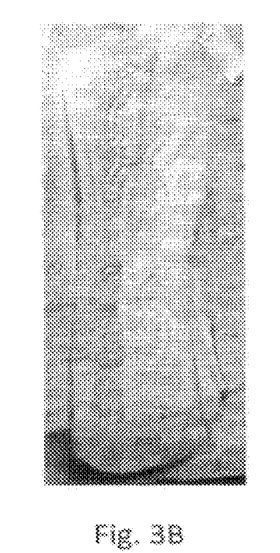
FIG. 3B demonstrates a photo of an absorbent article containing the ALM1 formulation 30 min following contact with urine.

The clear and sharp detection with ALM1 is further demonstrated in FIGS. 3A and 3B. FIG. 3A presents the dark stain obtained after contacting the composition of ALM1 absorbed into a panty shield with amniotic fluid (the dark stain is surrounded by a dashed line and an arrow is pointing at the stain). The dark stain presented in FIG. 3A is clearer and much more pronounced compared to the stains observed after contacting the reference compositions, namely, AL-SENSE and AmniScreen, with amniotic fluid. FIG. 3B presents a corresponding composition of ALM1 absorbed into a panty shield after being in contact with urine. As can be seen, no staining is observed indicating the absence of amniotic fluid.

TABLE 4

Readings of the candidate devices when exposed to urine, over time

| | 0-2 m | | 5 m | | 10 m | | 15 m | | 20 m | | 30 m | | 60 m | | 120 m | |
|---|---|---|---|---|---|---|---|---|---|---|---|---|---|---|---|---|
| | N | % | N | % | N | % | N | % | N | % | N | % | N | % | N | % |
| ALM1 | | | | | | | | | | | | | | | | |
| Negative | 58 | 81.7 | 60 | 84.5 | 62 | 87.3 | 62 | 87.3 | 62 | 87.3 | 64 | 90.1 | 64 | 90.1 | 64 | 90.1 |
| Positive | 13 | 18.3 | 11 | 15.5 | 9 | 12.7 | 9 | 12.7 | 9 | 12.7 | 7 | 9.9 | 7 | 9.9 | 7 | 9.9 |
| ALM2 | | | | | | | | | | | | | | | | |
| Negative | 53 | 74.6 | 57 | 80.3 | 60 | 84.5 | 60 | 84.5 | 61 | 85.9 | 62 | 87.3 | 62 | 87.3 | 62 | 87.3 |
| Positive | 18 | 25.4 | 14 | 19.7 | 11 | 15.5 | 11 | 15.5 | 10 | 14.1 | 9 | 12.7 | 9 | 12.7 | 9 | 12.7 |
| ALM3 | | | | | | | | | | | | | | | | |
| Negative | 52 | 73.2 | 56 | 78.9 | 60 | 84.5 | 61 | 85.9 | 61 | 85.9 | 64 | 90.1 | 64 | 90.1 | 64 | 90.1 |
| Positive | 19 | 26.8 | 15 | 21.1 | 11 | 15.5 | 10 | 14.1 | 10 | 14.1 | 7 | 9.9 | 7 | 9.9 | 7 | 9.9 |
| ALM4 | | | | | | | | | | | | | | | | |
| Negative | 57 | 80.3 | 60 | 84.5 | 60 | 84.5 | 61 | 85.9 | 60 | 84.5 | 61 | 85.9 | 61 | 85.9 | 61 | 85.9 |
| Positive | 14 | 19.7 | 11 | 15.5 | 11 | 15.5 | 10 | 14.1 | 11 | 15.5 | 10 | 14.1 | 10 | 14.1 | 10 | 14.1 |
| ALM1G | | | | | | | | | | | | | | | | |
| Negative | 58 | 81.7 | 60 | 84.5 | 62 | 87.3 | 63 | 88.7 | 63 | 88.7 | 65 | 91.5 | 65 | 91.5 | 65 | 91.5 |
| Positive | 13 | 18.3 | 11 | 15.5 | 9 | 12.7 | 8 | 11.3 | 8 | 11.3 | 6 | 8.5 | 6 | 8.5 | 6 | 8.5 |

TABLE 4-continued

Readings of the candidate devices when exposed to urine, over time

| | 0-2 m | | 5 m | | 10 m | | 15 m | | 20 m | | 30 m | | 60 m | | 120 m | |
|---|---|---|---|---|---|---|---|---|---|---|---|---|---|---|---|---|
| | N | % | N | % | N | % | N | % | N | % | N | % | N | % | N | % |
| ALM2G | | | | | | | | | | | | | | | | |
| Negative | 56 | 78.9 | 59 | 83.1 | 61 | 85.9 | 61 | 85.9 | 61 | 85.9 | 63 | 88.7 | 63 | 88.7 | 63 | 88.7 |
| Positive | 15 | 21.1 | 12 | 16.9 | 10 | 14.1 | 10 | 14.1 | 10 | 14.1 | 8 | 11.3 | 8 | 11.3 | 8 | 11.3 |
| ALM3G | | | | | | | | | | | | | | | | |
| Negative | 56 | 78.9 | 59 | 83.1 | 61 | 85.9 | 62 | 87.3 | 63 | 88.7 | 64 | 90.1 | 64 | 90.1 | 64 | 90.1 |
| Positive | 15 | 21.1 | 12 | 16.9 | 10 | 14.1 | 9 | 12.7 | 8 | 11.3 | 7 | 9.9 | 7 | 9.9 | 7 | 9.9 |
| ALM4G | | | | | | | | | | | | | | | | |
| Negative | 56 | 78.9 | 58 | 81.7 | 60 | 84.5 | 60 | 84.5 | 61 | 85.9 | 63 | 88.7 | 63 | 88.7 | 63 | 88.7 |
| Positive | 15 | 21.1 | 13 | 18.3 | 11 | 15.5 | 11 | 15.5 | 10 | 14.1 | 8 | 11.3 | 8 | 11.3 | 8 | 11.3 |

'%'—% sensitivity; 'N'—the number of samples tested; 'm'—minutes.

TABLE 5

Sensitivity of the candidate and reference pads

| Device | n/N | Sensitivity (%) | Lower 90% CL |
|---|---|---|---|
| ALM1 5 min | 20/20 | 100.0% | 86.09% |
| ALM1 10 min | 20/20 | 100.0% | 86.09% |
| AL-Sense 10 min | 18/20 | 90.0% | 71.74% |
| AmniScreen 30 min | 20/20 | 100.0% | 86.09% |

TABLE 6

Specificity of the candidate and reference pads

| Device | n/N | Specificity (%) | Lower 90% CL | P-Value vs. AmniScreen | P-Value vs. AL-SENSE |
|---|---|---|---|---|---|
| ALM1 5 min | 60/71 | 84.51% | 75.66% | 0.0588 | 0.0196 |
| ALM1 10 min | 62/71 | 87.32% | 78.92% | 0.0082 | 0.0067 |
| AL-SENSE 10 min | 53/71 | 74.65% | 64.76% | 0.5637 | NR |
| AmniScreen 30 min | 55/71 | 77.46% | 67.81% | NR | 0.5637 |

The clear and sharp detection with ALM1 is further demonstrated in FIGS. 3A and 3B. FIG. 3A presents the dark stain obtained immediately after contacting the composition of ALM1 absorbed into a panty shield with amniotic fluid (the dark stain is surrounded by a dashed line and an arrow is pointing at the stain). The dark stain presented in FIG. 3A is clearer and much more pronounced compared to the stains observed after contacting the reference compositions, namely, AL-SENSE and AmniScreen, with amniotic fluid. FIG. 3B presents a corresponding composition of ALM1 absorbed into a panty shield after being in contact with urine. As can be seen, no staining is observed indicating the absence of amniotic fluid.

Table 7 presents cross-tabulation readings of ALM1 and AL-SENSE along with the reading of AmniScreen—all readings were obtained on the same sample.

Table 8 displays the total percent agreement level of the candidate and the reference (AL-SENSE and AmniScreen) devices on positive and negative cases and overall with two-sided 95% exact confidence intervals for each. These values represent are the percent of cases in which the devices gave the same reading in amniotic fluid (positive cases; N=20), in urine (negative cases; N=71) and overall (together in both urine and amniotic fluid; N=91). As can be seen in the positive cases, i.e. amniotic fluid, ALM1 readings at 5 and 10 minutes correspond to AmniScreen readings. Thus, the agreement between ALM1 and AmniScreen in diagnosis of amniotic fluid is 100% for both time points, where agreement between ALM1 and AL-SENSE was only 90% (Table 5). In urine, ALM1 at 5 minutes agrees with AmniScreen in 98.2% of the cases and at 10 minutes in all (100%) cases where the AmniScreen provided a negative reading AmniScreen demonstrated six false positive readings at 5 minutes and seven false positive readings at 10 minutes while ALM1 correctly read negative reading at 5 minutes and 10 minutes (Table 6).

TABLE 7

Cross tabulation of candidate. AL-Sense versus AmniScreen

| | | AmniScreen | | | |
|---|---|---|---|---|---|
| | | Negative | | Positive | |
| Test Sample | | N | % | N | % |
| Amniotic Fluid | ALM1 5 m Positive | . | . | 20 | 100.0 |
| | ALM1 10 m Positive | . | . | 20 | 100.0 |
| | AL-SENSE Negative | . | . | 2 | 10.0 |
| | Positive | . | . | 18 | 90.0 |
| Urine | ALM1 5 m Negative | 54 | 98.2 | 6 | 37.5 |
| | Positive | 1 | 1.8 | 10 | 62.5 |
| | ALM1 10 m Negative | 55 | 100.0 | 7 | 43.8 |
| | Positive | . | . | 9 | 56.3 |
| | AL-SENSE Negative | 48 | 87.3 | 5 | 31.3 |
| | Positive | 7 | 12.7 | 11 | 68.8 |
| Overall | ALM1 5 m Negative | 54 | 98.2 | 6 | 16.7 |
| | Positive | 1 | 1.8 | 30 | 83.3 |
| | ALM1 10 m Negative | 55 | 100.0 | 7 | 19.4 |
| | Positive | . | . | 29 | 80.6 |
| | AL-SENSE Negative | 48 | 87.3 | 7 | 19.4 |
| | Positive | 7 | 12.7 | 29 | 80.6 |

In general, there was a disagreement between ALM1 at 5 min and 10 min and AmniScreen in seven cases out of which ALM1 gave the correct reading in six (6) cases at 5 min and in all seven (7) cases at the 10 min evaluation point. The differences were not statistically significant at 5 minutes (p=0.0588, Table 8) but were found statistically significant at 10 min (p=0.0082, Table 8). Stated otherwise, as evident from Table 7, the aforementioned disagreement is only on the negative cases (i.e., urine) where at 5 min ALM1 gave the correct reading in 6 of those 7 discrepant cases and in all 7 cases at the 10 min evaluation point. Disagreement between AL-SENSE and AmniScreen was greater—14 cases, of which the AmniScreen was correct in 9 of the cases. Despite the better accuracy, AmniScreen and AL-Sense were found to be similar (p=1.00, Table 8) with respect to percent of positive and negative readings yet less effective than ALM1.

TABLE 8

Agreement of ALM1 and AL-SENSE with AmniScreen

| | Device | n/N | Agreement Percent | Lower 95% CL | Upper 95% CL | P-Value McNemar's Test |
|---|---|---|---|---|---|---|
| Amniotic Fluid | ALM1 5 min | 20/20 | 100.0% | 83.16% | 100.0% | — |
| | ALM1 10 min | 20/20 | 100.0% | 83.16% | 100.0% | — |
| | AL-Sense | 18/20 | 90.0% | 68.30% | 99.98% | — |
| Urine | ALM1 5 min | 64/71 | 90.14% | 80.74% | 95.94% | — |
| | ALM1 10 min | 64/71 | 90.14% | 80.74% | 95.94% | — |
| | AL-Sense | 59/71 | 83.10% | 72.34% | 90.95% | — |
| Overall | ALM1 5 min | 84/91 | 92.31% | 84.79% | 96.85% | 0.0588 |
| | ALM1 10 min | 84/91 | 92.31% | 84.79% | 96.85% | 0.0082 |
| | AL-Sense | 77/91 | 84.62% | 75.54% | 91.33% | 1.000 |

Example 2: Clinical Study with Articles Lacking Surfactants and Acids

Two formulations, 3Mar1 and 3Mar2, were prepared, containing all of the ingredients of the ALM1 formulation aside from poloxamer 407 or salicylic acid (Table 9).

TABLE 9

Formulations Lacking Surfactants or Acids

| Ingredient | ALM1 | 3Mar1 | 3Mar2 |
|---|---|---|---|
| Cellulose Acetate | 2.00 | 2.50 | 2.50 |
| Cellulose acetate butyrate | 0.80 | 1.00 | 1.00 |
| Triethyl citrate | 1.00 | 1.00 | 1.00 |
| TDMAC | 0.053 | 0.053 | 0.053 |
| Poloxamer 407 | 0.30 | 0.30 | |
| Salicylic acid | 0.30 | | 0.30 |
| Nitrazine Yellow | 0.024 | 0.024 | 0.024 |

Urine samples (400 μl) having pH 7.0 were dripped on articles containing the 3Mar1 and 3Mar2 formulations and on an article containing the ALM1 formulation.

Figure 2:
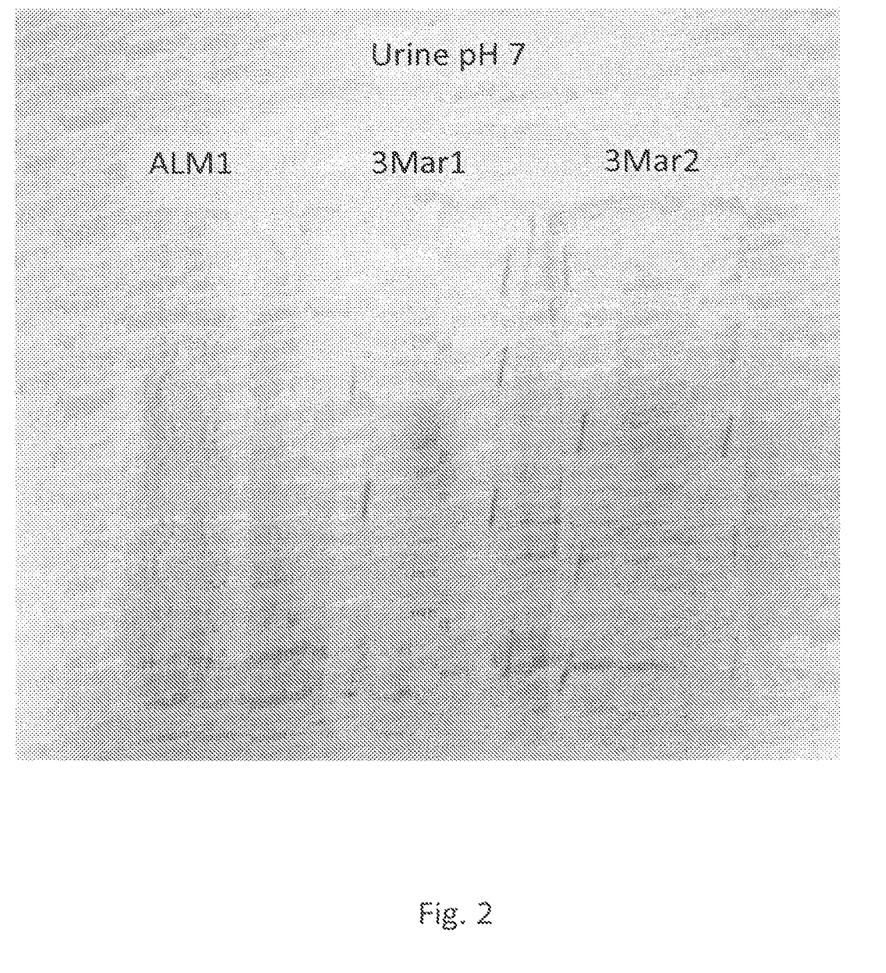
FIG. 2 exhibits the results obtained from contacting urine samples (pH 7) with one articles encompassing candidate composition—ALM1 and test compositions 3Mar1 and 3Mar2.

As shown in FIG. 2, following contact with urine each of the articles containing the 3Mar1 or the 3Mar2 formulations produced a false positive result, namely, a dark distinctive (blue) stain formed at the center of each of the articles. However, the ALM1 article provided a true negative result as it did not produce any stain upon contacting the urine sample.

The results indicate that surfactant(s) and acid(s) are required for obtaining a reliable detection.

Example 3: Feasibility of Wearing Study

A primary efficacy analysis with an article which includes the diagnostic composition ALM1 (also termed hereinafter "AL SENSE Blue") was conducted on a total of 43 women who were compliant with the study protocol and had valid data for the analysis. The analysis consists of a comparison between the patient's reading of the AL-SENSE Blue result and the clinical diagnosis.

Table 10 presents the subject's reading of the AL-SENSE Blue device versus the clinical diagnosis (sterile speculum Pooling test, if result was negative, then a microscopic Ferning test and pH test were performed).

TABLE 10

Subject's reading vs. clinical diagnosis

| Clinical Diagnosis | AL-SENSE Blue Subject's reading | | |
|---|---|---|---|
| Frequency (N) | Positive | Negative | Total |
| Negative | 1 | 16 | 17 |
| Positive | 25 | 1 | 26 |
| Total | 26 | 17 | 43 |

The sensitivity observed in this study is 96.15% (25/26) with a 95% exact binomial confidence interval of 80.36%-99.90% and the specificity is 94.12% (16/17) with a 95% exact binomial confidence interval of 71.31%-99.85%. Since the Success Criteria were 91% for the sensitivity and 73% for the specificity, it is concluded that the study was successful.

In a Secondary Efficacy study the women (all participants) were requested to complete a questionnaire. The first three questions were rated on a scale of 1 through 5, where 1 represents a poor result and 5 a very satisfactory result. The last two questions relate to patient's comprehension of the results reading. Tables 11-14 present in a descriptive manner the distributions of response gathered.

TABLE 11

Responses to Question 1
Is the Blue-Green Stain on the Indicator Strip Clear to Distinguish? (N = 35)

| Response | Frequency | % |
|---|---|---|
| Slightly Clear | 1 | 2.86 |
| Somewhat Clear | 10 | 28.57 |
| Clear | 17 | 48.57 |
| Very Clear | 7 | 20 |

TABLE 12

Responses to Question 2:
Is the pad comfortable for use? (N = 40)

| Response | Frequency | % |
|---|---|---|
| Quite Comfortable | 24 | 60 |
| Very Comfortable | 16 | 40 |

TABLE 13

Responses to Question 3
Did you experience any discomfort related to use of the pad? (N = 41)

| Response | Frequency | % |
|---|---|---|
| Indifferent | 17 | 41.46 |
| I was quite comfortable with the AL-SENSE Blue | 11 | 26.83 |
| I experienced no discomfort related to the AL-SENSE Blue | 13 | 31.71 |

TABLE 14

Responses to Question 4
According to the color of the used indicator strip and to the instructions leaflet, do you understand the cause of your wetness sensation? (N = 41)

| Response | Frequency | % |
|---|---|---|
| Amniotic fluid leakage | 23 | 53.66 |
| Urine leakage | 0 | 0 |
| Nothing | 7 | 17.07 |
| I don't know | 11 | 29.27 |

Of the 35 women that responded to question 1, 97.14% (34/35) responded that the Blue or green stain on the yellow strip was somewhat clear, clear or very clear to distinguish.

Of the 40 women that responded to question 2, 100% (40/40) responded the pad was quite or very comfortable for use.

Of the 41 women that responded to question 3, no one claimed that they had experienced even slight discomfort relating to the use of the AL-SENSE Blue.

Of the 41 women that responded to question 4, 24 marked their reading as positive. 95.83% of these women (23/24) stated that from the strip they had understood that the cause of their wetness was due to amniotic fluid leakage, all of them actually marked their reading as positive.

'Time to Reading' of the tested article was improved relative to the reference articles. Specifically, reading of the liner color was detected and recorded at 2, 5, 10, 15, 20 and 30 minutes (Table 15). In 100% (43/43) of the cases the final reading was already present from 2 minutes after exposition. In contrast, the Time to Reading of the reference article AmniScreen is 30 minutes while the Time to Reading of the reference article AL-SENSE is at least 10 minutes.

TABLE 15

Listing of the readings over time

| Subject Number | Patient result 0-2 min | Patient result 5 min | patient result 10 min | Patient result 15 min | Patient result 20 min | Patient result 30 min |
|---|---|---|---|---|---|---|
| 9200 | Positive | Positive | Positive | Positive | Positive | Positive |
| 9201 | Positive | Positive | Positive | Positive | Positive | Positive |
| 9202 | Positive | Positive | Positive | Positive | Positive | Positive |
| 9203 | Negative | Negative | Negative | Negative | Negative | Negative |
| 9204 | Positive | Positive | Positive | Positive | Positive | Positive |
| 9205 | Positive | Positive | Positive | Positive | Positive | Positive |
| 9206 | Negative | Negative | Negative | Negative | Negative | Negative |
| 9207 | Positive | Positive | Positive | Positive | Positive | Positive |
| 9208 | Positive | Positive | Positive | Positive | Positive | Positive |
| 9209 | Positive | Positive | Positive | Positive | Positive | Positive |
| 9210 | Positive | Positive | Positive | Positive | Positive | Positive |
| 9212 | Negative | Negative | Negative | Negative | Negative | Negative |
| 9213 | Negative | Negative | Negative | Negative | Negative | Negative |
| 9214 | Negative | Negative | Negative | Negative | Negative | Negative |
| 9215 | Negative | Negative | Negative | Negative | Negative | Negative |
| 9217 | Positive | Positive | Positive | Positive | Positive | Positive |
| 9218 | Positive | Positive | Positive | Positive | Positive | Positive |
| 9219 | Positive | Positive | Positive | Positive | Positive | Positive |
| 9222 | Positive | Positive | Positive | Positive | Positive | Positive |
| 9223 | Positive | Positive | Positive | Positive | Positive | Positive |
| 9224 | Positive | Positive | Positive | Positive | Positive | Positive |
| 9226 | Negative | Negative | Negative | Negative | Negative | Negative |
| 9227 | Positive | Positive | Positive | Positive | Positive | Positive |
| 9228 | Negative | Negative | Negative | Negative | Negative | Negative |
| 9229 | Negative | Negative | Negative | Negative | Negative | Negative |
| 9230 | Positive | Positive | Positive | Positive | Positive | Positive |
| 9231 | Positive | Positive | Positive | Positive | Positive | Positive |
| 9232 | Positive | Positive | Positive | Positive | Positive | Positive |
| 9233 | Negative | Negative | Negative | Negative | Negative | Negative |
| 9234 | Negative | Negative | Negative | Negative | Negative | Negative |
| 9237 | Positive | Positive | Positive | Positive | Positive | Positive |
| 9238 | Negative | Negative | Negative | Negative | Negative | Negative |
| 9239 | Negative | Negative | Negative | Negative | Negative | Negative |
| 9240 | Negative | Negative | Negative | Negative | Negative | Negative |
| 9241 | Negative | Negative | Negative | Negative | Negative | Negative |
| 9242 | Positive | Positive | Positive | Positive | Positive | Positive |
| 9243 | Negative | Negative | Negative | Negative | Negative | Negative |
| 9244 | Negative | Negative | Negative | Negative | Negative | Negative |
| 9246 | Positive | Positive | Positive | Positive | Positive | Positive |
| 9247 | Positive | Positive | Positive | Positive | Positive | Positive |
| 9248 | Positive | Positive | Positive | Positive | Positive | Positive |

TABLE 15-continued

Listing of the readings over time

| Subject Number | Patient result 0-2 min | Patient result 5 min | patient result 10 min | Patient result 15 min | Patient result 20 min | Patient result 30 min |
|---|---|---|---|---|---|---|
| 7189 | Positive | Positive | Positive | Positive | Positive | Positive |
| 7190 | Positive | Positive | Positive | Positive | Positive | Positive |

In summary of the primary and secondary studies, the AL-SENSE Blue subject reading sensitivity is 96.15%, which is very good for a home use test. Furthermore, the performance altogether (sensitivity, specificity, time of reading etc.) of AL-SENSE Blue is better than that of the reference articles AL-SENSE and AmniScreen.

Example 4: Article Preparation

Article preparation initially involved preparing each of the candidate and reference (including 3Mar1 and 3Mar2) formulations in the form of solutions. For this purpose, the solid part of each formulation, excluding Nitrazine yellow, was dissolved in 50 ml acetone. Nitrazine yellow was dissolved in 2 ml water and then added to the acetone solution.

The resulting solutions were sprayed on a substrate material. As a result, the substrate material acquired a faint yellow color, which gave a suitable background for the detection of a color change due to interaction with vaginal fluids, particularly, for the detection of a blue stain as a proper result of interaction with amniotic fluid. Each substrate was then integrated with a pre-formed panty liner, thereby obtaining a distinct diagnostic (candidate or reference) panty liner.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An indicator composition for detecting amniotic fluid in vaginal secretion, the indicator composition comprising:
   a plurality of polymers;
   a non-cyclic plasticizer;
   a hydrophilic surfactant;
   an aromatic carboxylic acid;
   an ion-balance reagent; and
   an indicator agent.

2. The indicator composition of claim 1, wherein the aromatic carboxylic acid includes salicylic acid, benzoic acid, or a combination thereof.

3. The indicator composition of claim 1, wherein the aromatic carboxylic acid includes salicylic acid.

4. The indicator composition of claim 1, wherein the hydrophilic surfactant includes a non-ionic surfactant.

5. The indicator composition of claim 1, wherein the hydrophilic surfactant includes a polymer.

6. The indicator composition of claim 5, wherein the hydrophilic surfactant includes a block copolymer surfactant.

7. The indicator composition of claim 1, wherein the indicator agent is negatively charged.

8. The indicator composition of claim 1, wherein the ion-balance reagent includes a quaternary ammonium salt.

9. The indicator composition of claim 1, wherein the non-cyclic plasticizer includes a tri-ester plasticizer.

10. The indicator composition of claim 1, consisting of the plurality of polymers; the non-cyclic plasticizer; the hydrophilic surfactant; the aromatic carboxylic acid; the ion-balance reagent; and the indicator agent.

11. An article for detecting the amniotic fluid in the vaginal secretion, the article comprising:
    an absorbent material for absorbing a biological fluid secreted from a person; and
    the indicator composition of claim 1.

12. The article of claim 11, wherein the absorbent material includes at least one member selected from the group consisting of a swab, a gauze, a panty shield, a hygienic napkin, diaper, and an interlabial absorbent structure.

13. The article of claim 11, wherein the aromatic carboxylic acid includes salicylic acid, benzoic acid, or a combination thereof.

14. The article of claim 11, wherein the aromatic carboxylic acid includes salicylic acid.

15. A method for diagnosing amniotic fluid leakage in vaginal secretion, the method comprising:
    positioning a secretion-monitoring article to receive a biological fluid secreted from a subject, the secretion-monitoring article comprising an indicator composition including a plurality of polymers; a non-cyclic plasticizer; a hydrophilic surfactant; an aromatic carboxylic acid; an ion-balance reagent; and an indicator agent;
    contacting the secretion-monitoring article with the vaginal secretion; and
    viewing the article, wherein a color change indicates the presence of amniotic fluid.

16. The method of claim 15, wherein the color change is a dark stain relative to the background of the secretion monitoring article.

17. The method of claim 16, wherein the dark stain is a dark blue stain or a dark green stain.

18. The method of claim 15, wherein the viewing is performed within less than 10 minutes after the contacting.

19. The method of claim 18, wherein the viewing is performed within less than 5 minutes after the contacting.

20. The method of claim 15, wherein the indicator composition is consisting of the plurality of polymers; the non-cyclic plasticizer; the hydrophilic surfactant; the aromatic carboxylic acid; the ion-balance reagent; and the indicator agent.

* * * * *